United States Patent [19]

Schatz

[11] 4,355,539
[45] Oct. 26, 1982

[54] FLUID SAMPLING PROBE

[75] Inventor: Klaus W. Schatz, Philadelphia, Pa.

[73] Assignee: Mobil Oil Corporation, New York, N.Y.

[21] Appl. No.: 221,483

[22] Filed: Dec. 30, 1980

[51] Int. Cl.³ .............................................. G01N 1/22
[52] U.S. Cl. .............................. 73/863.11; 73/864.73
[58] Field of Search ............ 73/863.11, 863.12, 190 R

[56] References Cited

U.S. PATENT DOCUMENTS

| | | | |
|---|---|---|---|
| 2,356,845 | 8/1944 | Hines | 73/863.12 |
| 3,301,059 | 1/1967 | Haas | 73/190 R |
| 3,592,562 | 7/1971 | Spliethoff | 73/863.12 |

Primary Examiner—S. Clement Swisher
Attorney, Agent, or Firm—Charles A. Huggett; Michael G. Gilman; George W. Hager

[57] ABSTRACT

A fluid sampling probe includes a fluid sampling conduit surrounded by a sheath. Cooling fluid passes through the annulus between the fluid sampling conduit and the sheath to cool the fluid samples passing through the fluid sampling conduit. A thermocouple has its sensing end located in the annulus to monitor the temperature of the cooling fluid.

3 Claims, 2 Drawing Figures

FLUID SAMPLING PROBE

BACKGROUND OF THE INVENTION

The field of catalytic cracking of petroleum hydrocarbons in a reaction vessel makes possible increased yield of desired end products. Such catalytic cracking particularly increases the yield of gasoline per barrel of the crude petroleum. This has been accomplished in large measure by cracking some of the heavier fractions of the crude petroleum into fuels boiling in the gasoline range. Such cracking of heavy distillates can be accomplished by subjecting the crude petroleum to heat and pressure in a closed vessel.

Although the types of compounds obtained in the cracking operation and the yields of suitable stocks are affected by all the interrelated variables, profound effects are produced by cracking in the presence of specific catalysts. The catalyst not only modifies the types of products produced in the cracking operation, but enables the reaction to be performed at reduced pressure and temperature.

Such cracking of petroleum hydrocarbons has been made into a continuous process wherein the catalyst, in the form of a moving mass of particle size material, is passed continuously through and from a reaction vessel to a regeneration vessel, and then through and from the regeneration vessel to the reaction vessel. Consequently, knowledge of the conditions within the process makes possible the increased yield of desired end products and products of greater purity.

SUMMARY OF THE INVENTION

In accordance with the present invention, there is provided a sampling probe for obtaining and cooling high temperature fluid samples.

More particularly, the probe obtains catalyst and gas samples from the regeneration unit of a petroleum catalytic cracking operation. The probe provides a conduit through which the catalyst and gas samples pass from the regeneration unit. A sheath surrounds the fluid sampling conduit along a portion of its length to form an annulus between the fluid sampling conduit and the sheath. A cooling fluid conduit provides cooling fluid flow through the annulus to cool the catalyst and gas samples flowing through the fluid sampling conduit. A thermocouple has its sensing end located within the annulus to provide a signal representative of the temperature of the cooling fluid. A deflector is provided adjacent the end of the annulus to deflect the cooling fluid exiting from the annulus away from the sampling end of the fluid sampling conduit.

DESCRIPTION OF THE PREFERRED EMBODIMENT

Figure 1:
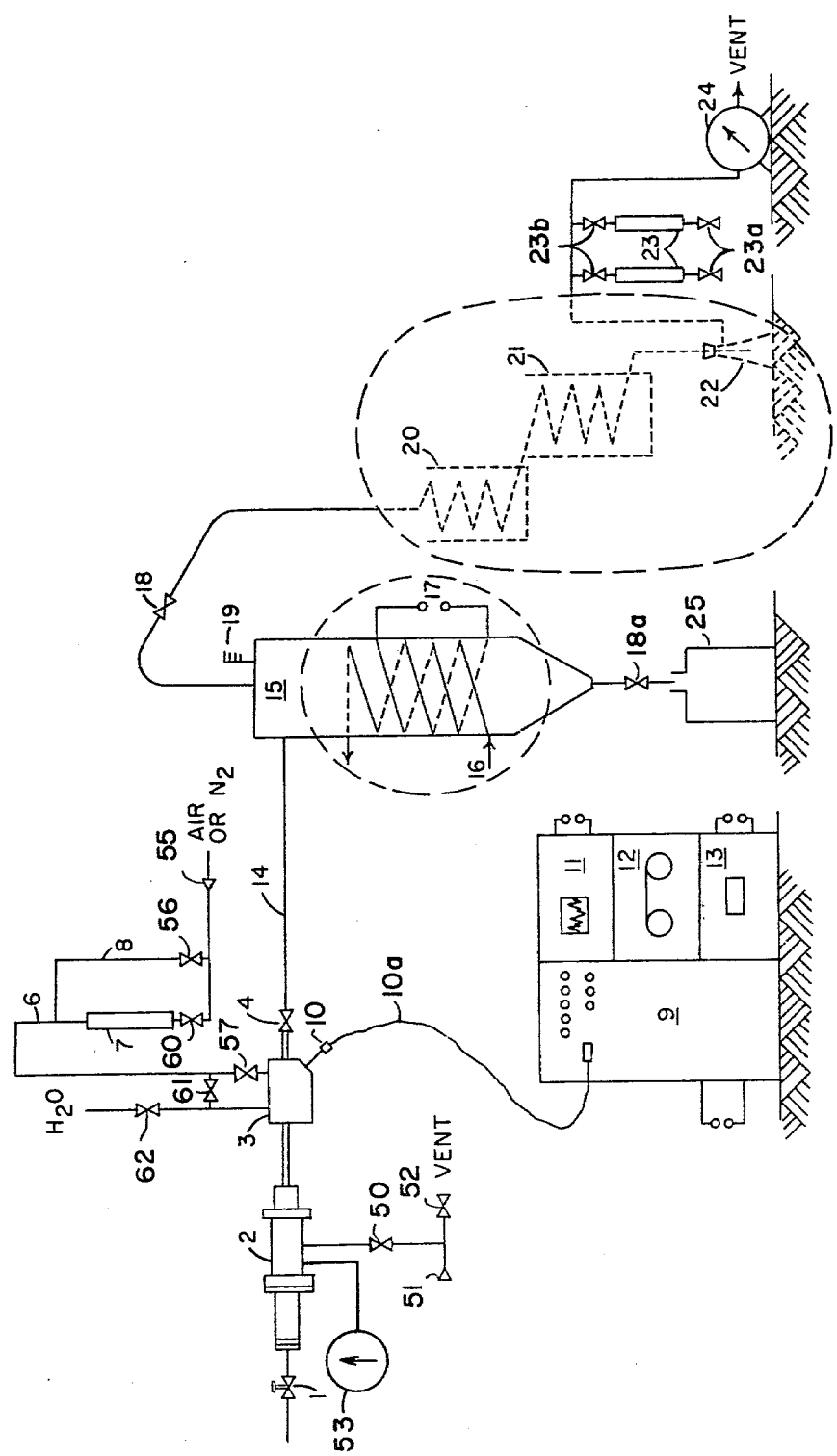
FIG. 1 is a diagrammatic arrangement of the catalyst and gas sampling system of the present invention.

The system in which the fluid sampling probe of the present invention finds applicability is illustrated in FIG. 1. The sampling of the catalyst-gas mixture takes place in the regeneration unit of a petroleum catalytic cracking system. The sampling normally takes place in the dense bed portion at the lower end of the regeneration unit. Samples could also be taken at the dilute phase zone of the regeneration unit.

The sampling probe 3 communicates with fluid catalyst-gas mixture through a stuffing box 2 and a gate valve 1. The probe 3 collects samples of the fluid and transmits such samples by way of conduit 14 into a cyclone separator 15 where the catalyst, the particulate matter, falls to the bottom and the gas samples flow through valve 18 to gas bombs or bottles 23.

One of the problems encountered in the analysis is due to the high temperatures at which the samples have been obtained giving rise to a continuing reaction which changes the gas constituents and contents between the time the sample is obtained at the probe end and the time the samples are collected for analysis.

In accordance with the present invention this difficulty is overcome by cooling the sample probe and hence the samples in order to significantly reduce and to a large measure avoid the continued reaction between the gas and the catalyst.

More particularly, the sample probe 3 is inserted through the stuffing box 2 to a point just short of the gate valve 1. At this time air is admitted by way of valve 50 from a suitable supply 51 into the stuffing box 2. The air pressure is adjusted by the venting of valve 52 so that approximately 50 psig is registered by the gauge 53. At this time air is now admitted from source 55 by way of valve 56, conduit 8, conduit 6 and valve 57 into the sample obtaining conduit of sampling probe 3. To assure that air is flowing through the system, the air from supply 55 is initially provided by way of valve 60 and air rotometer 7. The air rotometer 7 will indicate whether sufficient pressure has been applied to the system to permit flow through the sampling probe 3. Once flow has been established, the valve 60 may be closed and valve 56 open to permit air to flow by way of conduit 8. With air flowing in the system, valve 61 is opened to allow air flow into the annulus of the sampling probe 3.

Having established the flow of air through the various passageways of the sampling probe 3, the gate valve and adapter 1 is opened and the sampling probe 3 is inserted into the fluid stream of catalyst and gas. The supply of air from source 51 is then shut off.

Water is next admitted by way of valve 62 into the annulus of the sampling probe 3 and increased slowly while decreasing the amount of air being admitted through valve 61. The increase in water flow reduces the temperature at the end of sampling probe 3. When the temperature reaches a value of approximately 280° F. the desired water flow conditions have been met and air flow through valve 61 is cut off.

The probe is now conditioned to receive a sample of catalyst and gas. At this time valve 18 is opened. Air flow through valve 57 is cut off and valve 4 opened such that the catalyst and gas are forced through the sampling probe 3 and conduit 14 into the cyclone separator 15. Va2ve 18A at the base of the cyclone separator 15 is opened a short time later after catalyst has started to build up. The flow is by way of a pressure differential existing as between the atmospheric created pressure when valves 18 and 18A are open and the pressure in the catalyst stream of approximately 32 psi gauge.

After approximately ½ gallons of catalyst slop has accumulated in the collector 25, a second collector is set in place and the desired amount of catalyst accumulated.

At the same time, gas is being flowed out of the top of cyclone separator 15 through valve 18 and into the gas bomb bottles 23. These bottles are normally filled with water that has been saturated with regenerator flue gas.

When a sample is desired, valves 23a at the bottom are opened to bleed water from the bottles as gas accumulates. When valves 23b at the top of the water bombs 23 are opened the gas is admitted into the bombs displacing the water. When an adequate sample has been obtained all valves 23a and 23b are shut off.

Because the samples taken have been cooled there is no need for the prior art cooling and heating elements 16 and 17, respectively, shown on the cyclone separator as well as the prior art condensers 20 and 21 and the prior art liquid receiver 22 all shown in dashed lines in FIG. 1. However, cooling coil 16 and condensors 20 and 21 are needed to maintain constant dew point of gas sample if sampling probe is moved to another, hotter location in the regenerator where probe cooling becomes limiting.

The sampling probe 3 is designed for positioning at different radial points within the catalyst bed of the regeneration unit. Should the sample be desired at another location, the probe is positioned at the point and valve 57 opened to again permit air to flow through the probe and thus prevent any further samples from flowing through to the collector 25. Valve 4 is closed and another collector 25 is provided. At this time the air is cut off by closing valve 57 and valve 4 is opened to permit collecting of samples from a second point in the catalyst bed.

The temperature of the sampling probe 3 is detected by a thermocouple 10 whose output is applied by way of conductor 10a to a data logger 9 which contains an analog-to-digital converter. Data logger 9 converts the analog signal to a digital signal, preferably binary, which is then continuously recorded in binary form on a tape recorder 12. Instantaneous indication of the temperature at the end of the sampling probe 3 is provided by digital indicator 13. A visual indication of the analog signal is provided by applying the analog signal to the oscilloscope 11. The oscilloscope 11 and the tape recorder 12 are useful under those occasions where the temperature is varying rather rapidly at the end of the sampling probe 3, so rapidly in fact that the digital readout of indicator 13 is difficult to read. In that event the oscilloscope 11, which has memory capability, displays a waveform representing temperature variation over a short time which can be photographed and later studied. The recorder 12 enables one to collect data over a longer time. Typically a sampling rate of 500 readings per second is sufficient to properly represent the temperature fluctuations. Utilizing the data logger 9 and the associated recording and displaying equipment 11–13, the temperature measuring characteristics of the sampling probe 13 may be used to provide a temperature survey within the bed at different radial points and at different levels. While only one sampling probe 3 has been shown it will be understood that various probes can be utilized at different positions in the regeneration unit. With suitable multiplexing in data logger 9, a continuous recording can be obtained of temperature variations at those different positions.

Figure 2:
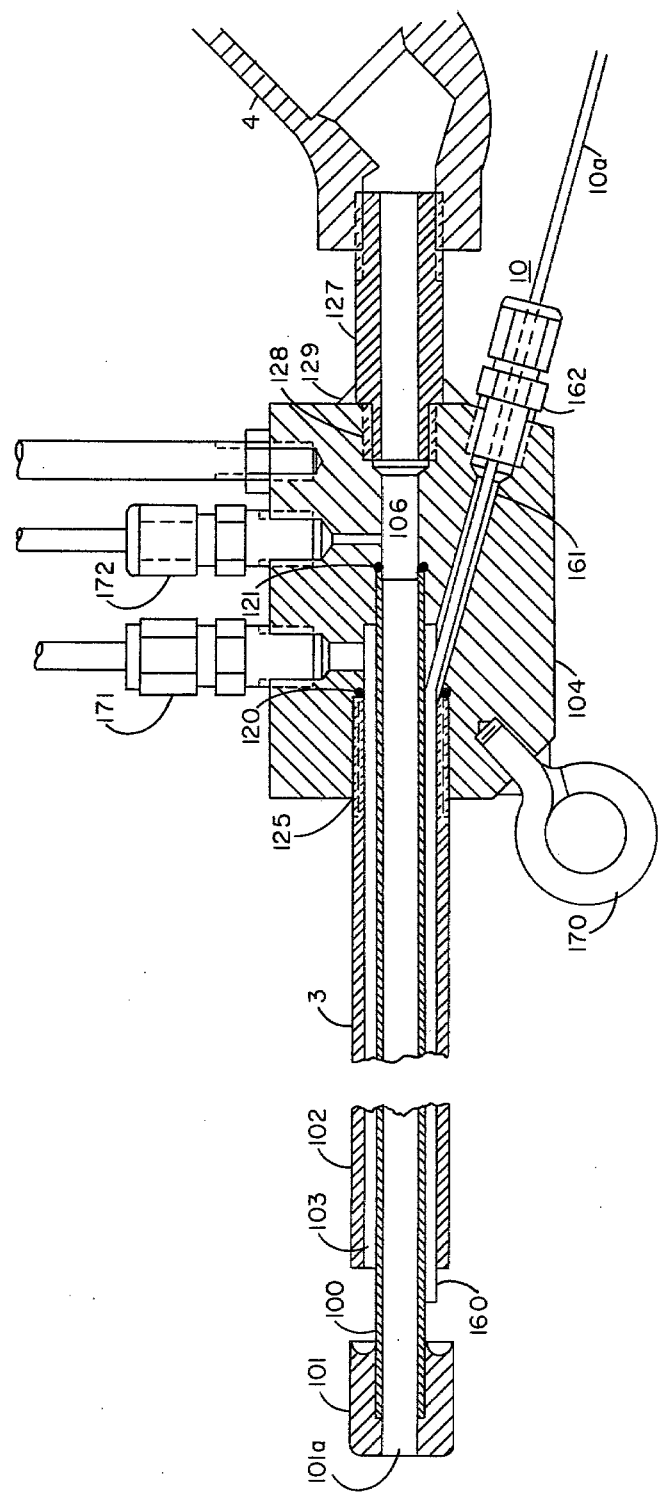
FIG. 2 is a sectional view of the catalyst and gas sampling probe of the system of FIG. 1.

Referring now to FIG. 2, there is shown details of the sampling probe 3 of the present invention. A probe head 101 is mounted at the end of a sampling conduit 100 by way of a screw type connection. The sampling conduit 100 is surrounded by a tubing or sheath 102 which together with the conduit provides an annulus 103. The sheath and the conduit are secured into a base 104 by way of thread connections.

Gaskets 120 and 121 are provided to prevent movement of catalyst and gas from the sampling conduit into the annulus by leakage. Gasket 120 prevents water from leaking through any space that might be present between the outer area of the sheath 102 and the contacting surface of base 104. Such leakage would result in water spraying out in the area of the stuffing box 2 of FIG. 1 through which the sampling probe 3 is inserted.

The base 104 is provided with a bore 106 which communicates to a pipe fitting 127 having one end screw fitted at 128 to the base 104. After the pipe fitting 127 has been connected, a weld 129 is provided peripherly to seal the pipe fitting 127 to the base 104 so as to prevent any gas or catalyst samples from escaping to the atmosphere.

A globe stop valve 4 is then screw fitted to the pipe fitting 127. This globe valve is identified in FIG. 1 as valve 4.

A thermocouple 10 has its sensing end immediately adjacent the outside surface of the sampling conduit 100. The thermocouple is threaded through a bore 161 provided in the base 104 and locked in position by fitting 162. The end of the thermocouple wire 10a is connected to the data logger 9.

It will be noted that the head 101 of the probe is of larger diameter than the sheath 102. This prevents the probe from being blown out through the stuffing box 2 assembly.

The probe head 101 is also machined at the end immediately adjacent the annulus 103 in order to provide for deflection of the water passing out of the annulus and into the regenerator and more specifically designed so that the flow is diverted away from the input 101a of the probe head.

The base 104 may be provided with an eye blot 170 to which may be attached a chain whose opposite end would be secured to an outside surface of the regenerator. This is a safety feature which would prevent the probe being forced out through the stuffing box 2 in the event the probe head 101 came loose from the end of the sampling conduit 100.

Standard gauge lock fittings 172 and 171 are provided to enable passage of air from valve 57 of FIG. 1 into the sampling conduit 100 and also to provide water and/or air passage by way of valve 61 into the annulus 103 respectively.

The entire sampling probe 3 may be made of stainless steel. This includes all the fittings as well as the connection to the globe stock valve 130 and base 104. Preferably it would be desirable to use a grade 410 stainless steel, because it does not have the disadvantage of having nickel in its composition which would catalyze CO to $CO_2$.

Although the present invention has been described in connection with a preferred embodiment, various modifications and changes may be nade without departing from the spirit and scope of the present invention as set forth in the appended claims.

What is claimed is:

1. A probe for obtaining high temperature fluid samples comprising:
   (a) a fluid sampling conduit through which the fluid samples pass,
   (b) a sheath surrounding said fluid sampling conduit along a portion of its length to form an annulus between said fluid sampling conduit and said sheath, (c) a supply of cooling fluid, (d) a cooling fluid conduit for providing cooling fluid flow through said annulus to cool the fluid samples flowing through said fluid sampling conduit, (e) a thermocouple having its sensing end located within said annulus to provide a signal representative of the temperature of said cooling fluid, and (f) means for deflecting the cooling fluid exiting from said annulus away from the sampling end of said fluid sampling conduit.

2. The sampling probe of claim 1 wherein said deflecting means comprises a probe head mounted about said fluid sampling conduit between its sampling end and the end of said sheath, said probe head being of greater diameter than said sheath so as to provide a deflecting surface for said cooling fluid as it passes out of the annulus between said sheath and said fluid sampling conduit.

3. The sampling probe of claim 2 wherein said probe head is machined along its surface adjacent the end of said sheath so as to provide a suitable deflecting surface for said cooling fluid.

* * * * *